United States Patent
Sessler

(10) Patent No.: US 6,648,841 B1
(45) Date of Patent: Nov. 18, 2003

(54) DEVICE FOR REANIMATING PATIENTS SUFFERING FROM CARDIAC ARREST

(76) Inventor: Stefan Sessler, Bilzer Weg 7, D-72474 Winterlingen (DE)

( * ) Notice: Subject to any disclaimer, the term of this patent is extended or adjusted under 35 U.S.C. 154(b) by 0 days.

(21) Appl. No.: 09/601,939

(22) PCT Filed: Nov. 16, 1999

(86) PCT No.: PCT/EP99/08810

§ 371 (c)(1),
(2), (4) Date: Aug. 10, 2000

(87) PCT Pub. No.: WO00/35404

PCT Pub. Date: Jun. 22, 2000

(30) Foreign Application Priority Data

Dec. 12, 1998 (DE) .......................... 198 57 421

(51) Int. Cl.[7] ............................................. A61H 31/02
(52) U.S. Cl. ........................................... 601/41; 601/43
(58) Field of Search .............................. 601/41, 42, 43, 601/44

(56) References Cited

U.S. PATENT DOCUMENTS

| 3,425,409 A | | 2/1969 | Isaacson | |
|---|---|---|---|---|
| 3,489,140 A | * | 1/1970 | Mullikin | 601/97 |
| 3,509,899 A | * | 5/1970 | Hewson | 137/87.04 |
| 3,512,522 A | | 5/1970 | Greenlee | |
| 3,782,371 A | * | 1/1974 | Derouineau | 601/41 |
| 3,965,893 A | | 6/1976 | Ragailler | |
| 5,257,619 A | | 11/1993 | Everett | |
| 5,327,887 A | | 7/1994 | Nowakowski | |

FOREIGN PATENT DOCUMENTS

| DE | 25 21 121 A | 11/1976 |
|---|---|---|
| FR | 1 331 573 | 5/1963 |
| FR | 2 382 889 | 10/1978 |

* cited by examiner

Primary Examiner—Nicholas D. Lucchesi
Assistant Examiner—Tam Nguyen
(74) Attorney, Agent, or Firm—Michael J. Striker

(57) ABSTRACT

A device (10) for resuscitating patients with cardiac arrest, having a lifting device, disposed on a carrier, for a ram that can be placed on the chest of the patient and can be moved up and down, or for a suction bell (15) with a ram (15.1), wherein the carrier is embodied as a gantry (16) that can be placed above the chest of the patient, and the gantry (16) is adjustable at least in width.

23 Claims, 4 Drawing Sheets

DEVICE FOR REANIMATING PATIENTS SUFFERING FROM CARDIAC ARREST

BACKGROUND OF THE INVENTION

The invention relates to a device for resuscitating patients with cardiac arrest, having a lifting device, disposed on a carrier, for a ram that can be placed on the chest of the patient and can be moved up and down, or for a suction bell with a ram.

The success of resuscitation after a cardiac arrest is as slight as ever. According to one statistic, fewer than 5% of patients survive long-term after resuscitation outside the hospital. The long-term success rate of resuscitation in the hospital is 10%. A major problem in resuscitation is that large proportions of the population know the technique of resuscitation only inadequately if at all. Even official members of such aid organizations as the German Red Cross (DRK) or the German Rescue Society (DLRG) are often quite unsure about using resuscitation procedures. In view of this, various resuscitation devices of the type defined at the outset have been developed and put on the market in the past. They include devices that are fastened to the patient with a cinch belt, or devices that are not fixed on the patient at all, or devices that have a board for placement under the patient so as to fix the device. A common feature of all these resuscitation devices is that either they are very hard to transport, because they are very large or very heavy, or they have an external energy supply, which sometimes means they are not usable in all locations.

The resuscitation devices known thus far operate by either the CPR method or the ACD method.

CPR is the standard method for resuscitation. A distinction is made between the one-person or-two-person method. In the one-person method, fifteen cardiac massages are performed, followed by two breaths blown in. In the two-person method, five cardiac massages are performed, followed by one breath blown in.

In the ACD method, after the compression of the chest, the chest is raised again with a suction bell. This act of decompression promotes venous return of the blood, which improves the effectiveness of the heart-lung resuscitation.

SUMMARY OF THE INVENTION

The object of the present invention is to improve a device for resuscitating patients with cardiac arrest in such a way that it is flexible and simple to handle.

The invention attains this stated object by means of a device of the type defined at the outset, in which the carrier is embodied as a gantry that can be placed above the chest of the patient, and the gantry is adjustable at least in width. As a result of this design, the resuscitation device can easily be fastened onto patients with different sizes of rib cage and can be used regardless of local conditions. The gantry construction of the carrier is also very stable, since with it it is possible for the device to be symmetrically supported on both sides of the patient.

Advantageously, the device can have an adjusting knob or handle with which the gantry can be adjusted at least in its width. Thus if it is vertically adjustable as well, the gantry can be adjusted in both width and height, with a single knob.

To prevent overly fast delivery of the respiration air in the artificial respiration process, the user-applied force acting on the ram or the suction bell can be increased, in particular by means of a spring and/or a nozzle.

As an abutment for the resuscitation device in actuating the lifting device, the gantry legs can be provided with feet, preferably embodied in wedgelike fashion. These feet are slipped under the patient's rib cage and thus prevent the entire device from being lifted when the chest is compressed by means of the ram or the suction bell.

Adapting the resuscitation device to different widths for different chests can for instance be done in that the traverse support of the gantry is embodied as a telescoping tube. In the telescoping tube and/or in the legs, a spring mechanism or a gear wheel and rack mechanism can be disposed above the patient for automatically centering the lifting device.

Alternatively to embodying the traverse support as a telescoping tube, the left and right traverse supports of the gantry, instead of being aligned in a single line, can be disposed offset from one another. Once again, this makes it possible to adjust the width of the gantry. Furthermore, for transport purposes, because of the offset disposition of the left and right traverse support, the device can be reduced in its external dimensions so sharply that it does not have to be taken apart.

With the offset disposition of the left and right traverse supports, the lifting device can advantageously be centered over the patient by means of a cable or chain mounted on the traverse supports.

To enable adjusting the resuscitation device individually to the height of the chest in different patients, the lifting device can be disposed vertically adjustably on the gantry. A vertical adjustment of the legs of the carrier would also be possible.

To make the resuscitation device independent of any external energy supply and nevertheless require less force of the helper, a step-up mechanism can be used. It can be converted as a lever or gear, or a hydraulic or pneumatic pressure step-up means, or the like. After actuation, the mechanism can return automatically to its basic position.

The lifting device can also have a lifting cylinder, which aspirates air from the environment that can be fed to the patient via a mask or a tube for artificial respiration of the patient. In this way, the resuscitation device can also be used for artificial respiration of the patient, independently of oxygen bottles. To allow both a mask and a tube to be used, the resuscitation device can have an adapter.

To prevent the air during a reciprocating motion from escaping downward toward the aspiration opening out of the cylinder, the lifting device can have a check valve, so that the air can escape only in the direction of the face mask or the tube.

To prevent mistakes by users, the device can advantageously alternate automatically between cardiac massage and artificial respiration modes. Depending on the particular application, it can be operated by the CPR method and/or the ACD method.

For patients with a large chest, a longer lifting distance has to be traversed than for people with a smaller chest. Furthermore, the tidal volume is equally dependent on the rib cage size. For this reason, the lifting distance for the cardiac massage and the tidal volume of the device can both be adjustable.

To allow even unskilled users of the resuscitation device to operate the device immediately and safely without having to pay attention to whatever size the patient's rib cage is, the lifting distance for the cardiac massage can be established automatically as a function of the vertical position of the lifting device. Mistakes in operation can be practically precluded by this provision.

To provide an indication of the lifting distance and the tidal volume that have been set, the device can have a scale for the lifting distance and the tidal volume. Advantageously, the resuscitation device can have an oxygen connection for an oxygen bottle or an oxygen reservoir placed in between.

To make it easy to transport, the device can expediently be capable of being taken apart.

Depending on the desired application, it can be used purely as a respirator or as a cardiac massage device.

To make the resuscitation device ready for use at all times even after long periods of non-use, it can be maintenance-free.

For hygienic reasons, the device can furthermore be capable of being sterilized by steam.

When the device is used by the ACD method, the suction bell can be extended past the height of the chest in the return stroke, in order to generate the requisite decompression.

To ease the work for users, the decompression force can be exerted by a spring which is prestressed in the compression stroke.

In the case of relatively weak springs, the decompression can be reinforced by a force-amplifying mechanism, such as a lever, or by means of external energy.

As already noted, the lifting device can be operated via a lever. It is especially advantageous if this lever is supported rotatably on the device, so that the device can be used from all sides or at least from several sides. The lever can be designed ot be lockable in certain angular positions in detent fashion. One such embodiment of the device also has advantages when it is used by left-handed persons. Even in tight spaces, for instance in the center aisle of an airplane, this kind of rotatably supported lever offers advantages.

Further advantages can be attained if the device has a switchover mechanism that switches over automatically from artificial respiration to cardiac massage and vice versa. A switchover mechanism of this kind can be realized in the form of a gear mechanism or a guide track.

As already noted, the tidal volume can be adjusted automatically as a function of the vertical position of the lifting device. An additional limitation can also be provided, in the form of a stop that makes it possible to generate a constant tidal volume, regardless of the rib cage size, and the depth of each compression can be either manually or automatically adjustable.

The device can also be expanded with a defibrillator, thus forming a combination unit for resuscitation. The data ascertained from the diagnosis of an automatic external defibrillator (AED) can be used, among other ways, for starting or ending the functions of the resuscitation device. In the case of this kind of expansion, the resuscitation device can function either with or without external energy.

An exemplary embodiment of a device according to the invention for resuscitating patients with cardiac arrest will be described in further detail below in conjunction with the accompanying drawing.

DESCRIPTION OF THE PREFERRED EMBODIMENTS

Figure 1:
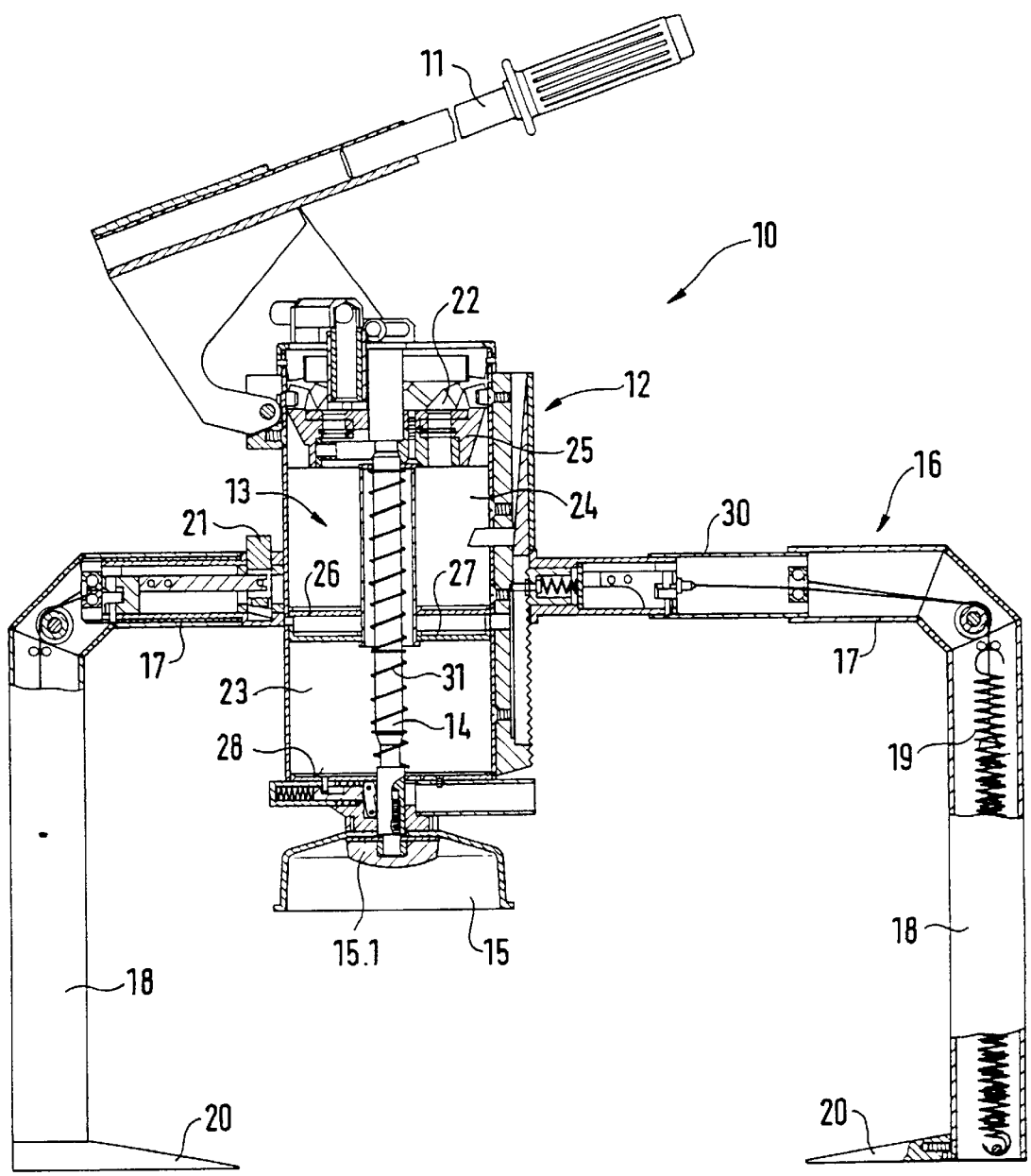
FIG. 1, a side view of a resuscitation device.
Figure 2:
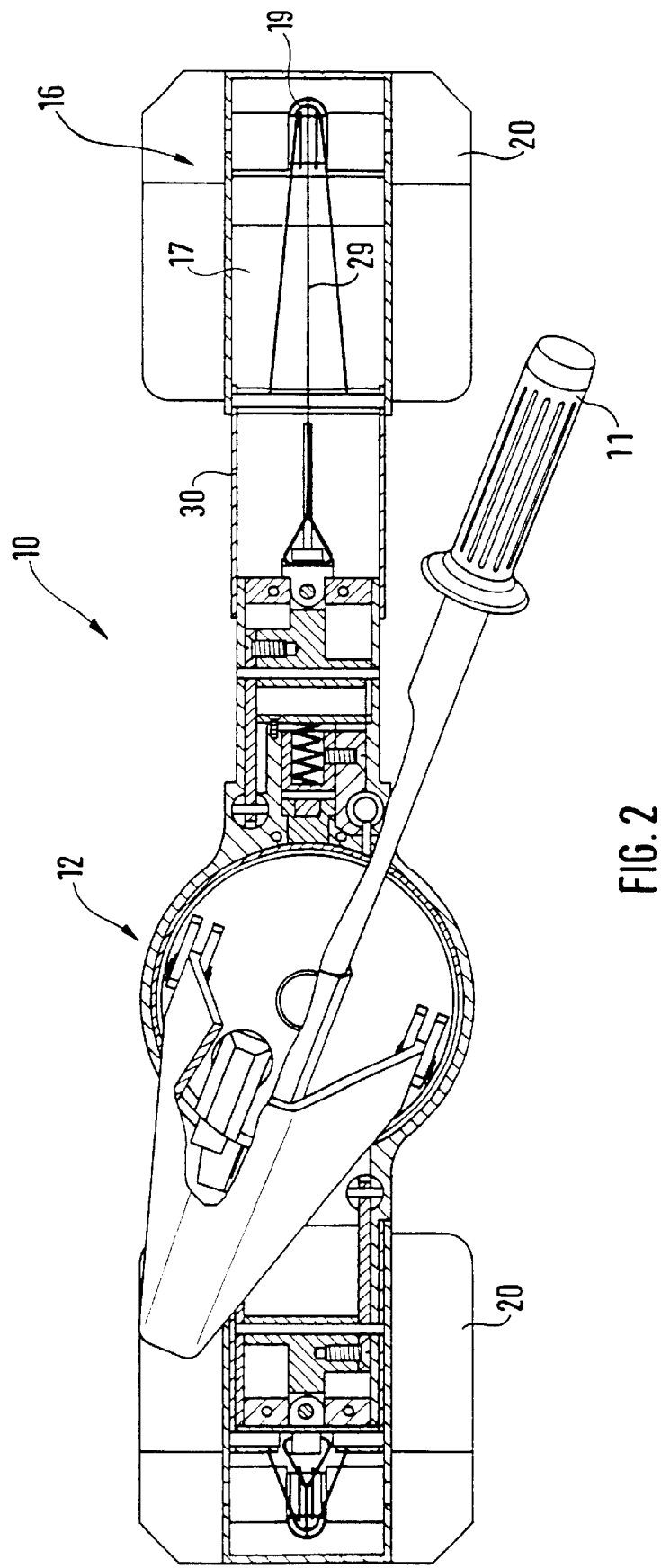
FIG. 2, a plan view on a resuscitation device of FIG. 1.

FIG. 1 shows a device 10 for resuscitating patients with cardiac arrest. A lifting device 12, which has a lifting cylinder 13, is actuated by means of the lever 11. It is accordingly actuated purely mechanically and is thus independent of external electrical, pneumatic or hydraulic energy. By means of a pressure rod 14, the lifting device 12 puts a suction bell 15 with a ram 15.1 into a periodic up and down motion. The ram 15.1 is seated in use on the thoracic pressure point of a patient, and a cardiac massage is performed on the patient by the up and down motion of the ram 15.1. Upon each return stroke, the chest is lifted by the suction bell 15. The lifting device 12 is disposed on a carrier in the form of a gantry 16. The gantry 16 has a traverse support 17, inside which a telescoping tube 30 is located. By means of the telescoping tube 30, the gantry 16 can be adjusted to the particular width of the chest of the patient to be treated. Springs 19 are accommodated in the gantry legs 18 and are coupled with the telescoping tube 30 via a cable 29 (FIG. 2). Since the springs 19 in the legs 18 are identical on the left and right, the lifting device 12 is automatically centered as the telescoping tube 30 is pulled apart. As a result, the suction bell 15 and the ram 15.1 are always located directly centrally to the chest of the patient. The gantry legs 18 stand on feet 20 that point inward. The feet 20 are wedgelike in embodiment and can thus be slipped easily under the patient's rib cage. During the treatment, the patient, because he is lying on the feet 20, thus fixes the device 10 by his own weight. To enable the device 10 to be transported in a portable case, the feet 20 can be hinged closed or released from the gantry legs 18 by simple manipulations, and the traverse supports 17 together with the gantry legs 18 can be released from the lifting device 12 by pressing on the unlocking knob 21. The device 10 can thus be taken apart quickly with only a few manipulations and easily stowed in the carrying case.

The device 10 can be used both for cardiac massage and for artificial respiration of the patient. By means of a detent disk 22, the ratio of respiration strokes to massage strokes can be determined. The lifting cylinder 13 has two chambers 23 and 24. The chamber 24 is defined at the top by a rotary piston 25 and at the bottom by a partition 26. The chamber 23 is defined at the top by a piston disk 27 and at the bottom by the cylinder bottom 28. Because the cylinder 13 is split into the two chambers 23 and 24, the entire volume of the cylinder 13 can be pumped into the lungs of the patient with a shorter motion of the lever 11.

FIG. 2 shows the device 10 of FIG. 1 from the top. Via the lever 11, the lifting device 12 is actuated, and by this means the cardiac massage is performed or the patient is supplied with air to breathe. A cable 29 that connects the spring 19 to the telescoping tube 30 extends inside the traverse support 17 of the gantry 16. The gantry 16 stands on the wide feet 20 that are slipped under the patient's body.

Figure 3:
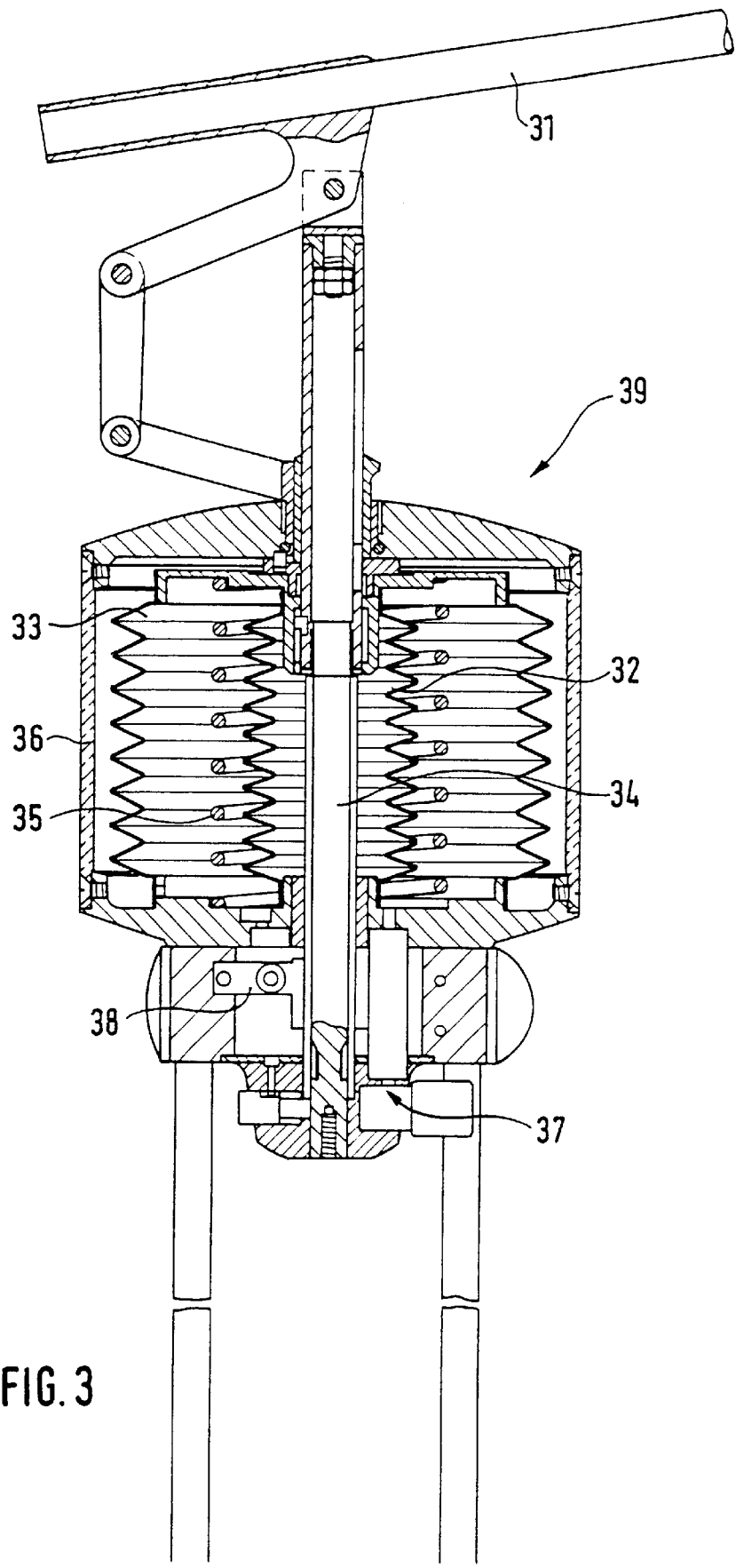
FIG. 3, an end view on a further embodiment of a resuscitation device.

FIG. 3 shows a device 39 for resuscitating patients with cardiac arrest. By means of the lever 31, the bellows 32 and 33 that determine the tidal volume are compressed, thus supplying the air for the patient to breathe. The inner bellows 32 has the task of separating a pressure rod 34 and the mechanism connected to it from the tidal volume. The outer bellows 33 partitions off the tidal volume from the outer environment. A spring 35 is disposed in the interior of the outer bellows 33 and forces the two bellows 32 and 33, which are in touch contact with one another at their bottoms and tops, apart again after the respiration stroke has been performed. The spring 35 also increases the user-applied force during artificial respiration, in order to prevent overly rapid delivery of the tidal volume. A nozzle 37 is also used to increase the user-applied force during the artificial respiration, by narrowing the cross section of the air conduit through which the air is delivered to the patient. A transparent protective cylinder 36 closes off the outer bellows 33 from the outside. Because of the transparent material of the protective cylinder 36, the user of the device 39 can observe the artificial respiration process. A stop wedge 38 limits the stroke of the pressure rod 34.

Figure 4:
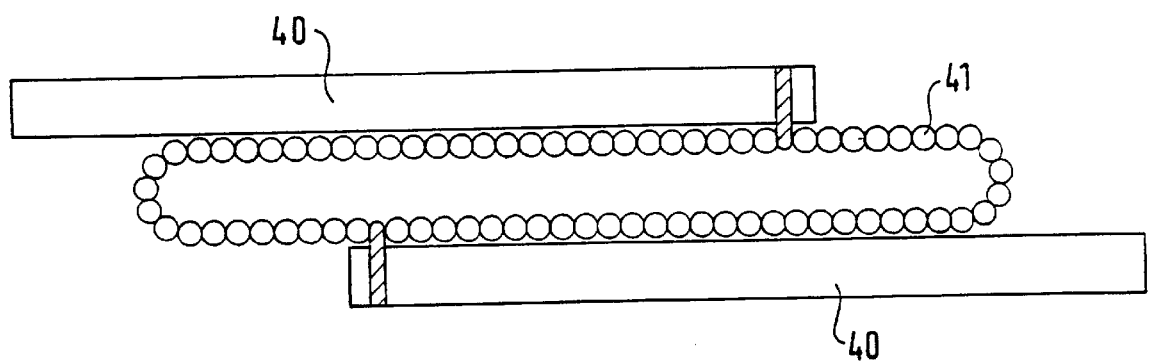
FIG. 4, a basic sketch of two traverse supports offset from one another.

FIG. 4 shows the basic disposition of the two traverse supports 40 offset from one another. They are displaceable in their longitudinal direction. The two traverse supports 40 are connected to one another by a closed revolving cable 41. By means of the closed revolving cable 41, the two traverse supports are at the same time displaced by the same distance to the left or to the right, and as a result when the two traverse supports 40 are pulled apart, the lifting device is centered precisely above the patient. Before use, the traverse supports 40 are pulled apart, and they are pushed back together again after use. Thus the entire device can be reduced in terms of its external dimensions so sharply that it need not be taken apart for transportation.

What is claimed is:

1. A device (10, 39) for resuscitating patients with cardiac arrest, having a lifting device (12), disposed on a carrier, for a ram that can be placed on the chest of the patient and can be moved up and down, or for a suction bell (15) with a ram (15.1), characterized in that the carrier is embodied as a gantry (16) that can be placed above the chest of the patient, and the gantry (16) is adjustable at least in width, wherein the telescoping tube (30) and/or the legs (18) have a spring mechanism (19) or a gear wheel and rack mechanism for automatic centering the lifting device (12) over the patient.

2. The device (10, 39) of claim 1, characterized in that it has an adjusting knob to enable adjusting the gantry at least in its width.

3. The device (10, 39) of claim 1, characterized in that the user-applied force acting on the ram (15.1) or the suction bell (15) can be increased, in particular by means of a spring (35) and/or a nozzle (37).

4. The device (10, 39) of one of claim 1, characterized in that the gantry legs (18) are provided with feet (20) pointed inward, which can be slipped under the rib cage of the patient.

5. The device (10, 39) of one of claim 1, characterized in that the traverse support (17) of the gantry (16) is embodied as a telescoping tube (30).

6. The device (10, 39) of one of claim 1, characterized in that the left and right traverse supports (40) of the gantry (16) are offset from one another.

7. The device (10, 39) of claim 1, characterized in that the lifting device (12) can be centered over the patient by means of a cable or chain mounted on the traverse supports (40).

8. The device (10, 39) of one of claim 1, characterized in that the lifting device (12) is disposed vertically adjustably on the gantry (16).

9. The device (10, 39) of one of claim 1, characterized in that the lifting device (12) is actuatable purely mechanically via a lever (11), a toothed gearing system, or other mechanical step-up means.

10. The device (10, 39) of one of claim 1, characterized in that the lifting device (12) has a lifting, cylinder (13), which aspirates air from the environment that can be fed to the patient via a mask or a tube for artificial respiration of the patient.

11. The device (10, 39) of one of claims 1, characterized in that it automatically alternates between cardiac massage and respiration.

12. The device (10, 39) of one of claim 1, characterized in that it can be operated by the CPR method and/or the ACD method.

13. The device (10, 39) of one of claim 1, characterized in that the lifting distance for the cardiac massage can be adjusted as a function of the size of the patient's rib cage.

14. The device (10, 39) of claim 3, characterized in that the lifting distance for the cardiac massage is established automatically and as a function of the vertical position of the lifting device (12).

15. The device (10, 39) of claim 1, characterized in that a tidal volume is adjustable as a function of the size of the patients rib cage.

16. The device (10, 39) of claim 1, characterized in that it has a scale for the lifting distance and a tidal volume.

17. The device (10, 39) of claim 1, characterized in that it has a scale for the lifting distance and a tidal volume.

18. The device (10, 39) of one of claim 1, characterized in that it can be taken apart for transport.

19. The device (10, 39) of one of claim 1, characterized in that it can be used purely as a respirator or as a cardiac massage device.

20. The device (10, 39) of one of claim 1, characterized in that it is steam-sterilizable.

21. The device (10, 39) of one of claim 1, characterized in that in operation of the device with a suction bell (15), the device can be moved in the reverse stroke to a level that is higher than the chest height.

22. The device (10, 39) of one of claim 1, characterized in that the decompression force of the suction bell (15) can be exerted by a spring (31) that can be prestressed in the compression stroke.

23. A device (10, 39) for resuscitating patients with cardiac arrest, having a lifting device (12), disposed on a carrier, for a ram that can be placed on the chest of the patient and can be moved up and down, or for a suction bell (15) with a ram (15.1), characterized in that the carrier is embodied as a gantry (16) that can be placed above the chest of the patient, and the gantry (16) is adjustable at least in width, wherein the telescoping tube (30) and/or the legs (18) have a spring mechanism (19) or a gear wheel and rack mechanism for automatic centering the lifting device (12) over the patient, so that when one of the legs is moved toward the body of a patient, also the other leg is moved toward the body of the patient.

* * * * *